United States Patent
Schulman et al.

(10) Patent No.: US 7,713,474 B2
(45) Date of Patent: May 11, 2010

(54) LIQUID PERMEABLE COMPOSITION IN DRY REAGENT DEVICES

(75) Inventors: Lloyd S. Schulman, Osceola, IN (US); Michael J. Pugia, Granger, IN (US); Spencer Lin, Yorktown Heights, NY (US); Karlheinz Hildenbrand, Krefeld (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1020 days.

(21) Appl. No.: 10/966,858

(22) Filed: Oct. 14, 2004

(65) Prior Publication Data

US 2005/0129572 A1    Jun. 16, 2005

Related U.S. Application Data

(63) Continuation-in-part of application No. 10/459,825, filed on Jun. 12, 2003, now abandoned, and a continuation-in-part of application No. PCT/IB03/00055, filed on Jan. 13, 2003.

(60) Provisional application No. 60/348,253, filed on Jan. 15, 2002.

(51) Int. Cl.
G01N 31/22 (2006.01)
G01N 31/00 (2006.01)

(52) U.S. Cl. .............. 422/58; 422/55; 422/50; 427/2.13; 427/2.11; 427/2.1

(58) Field of Classification Search .............. 422/58, 422/56, 57, 55, 50; 600/347; 427/2.13, 2.11, 427/2.1
See application file for complete search history.

(56) References Cited

U.S. PATENT DOCUMENTS

| | | | |
|---|---|---|---|
| 3,992,158 A | 11/1976 | Przybylowicz et al. | |
| 3,993,451 A | 11/1976 | Verbeck | |
| 4,356,149 A | 10/1982 | Kitajima et al. | |
| 4,452,887 A * | 6/1984 | Kitajima et al. | ............... 435/14 |
| 4,806,311 A | 2/1989 | Greenquist | |
| 4,824,640 A | 4/1989 | Heldenbrand et al. | |
| 5,079,140 A | 1/1992 | Albarella et al. | |
| 5,141,850 A | 8/1992 | Cole et al. | |
| 5,171,688 A | 12/1992 | Hewett et al. | |
| 5,360,595 A | 11/1994 | Bell et al. | |
| 5,393,493 A | 2/1995 | Makino et al. | |
| 5,736,335 A | 4/1998 | Emmons et al. | |
| 5,801,061 A | 9/1998 | Stepehnson | |
| 5,916,156 A | 6/1999 | Hildenbrand et al. | |
| 6,187,268 B1 | 2/2001 | Albarella | |

FOREIGN PATENT DOCUMENTS

| | | |
|---|---|---|
| EP | 0162302 | 11/1985 |
| EP | 0226465 A2 | 6/1987 |
| GB | 2085159 | 4/1982 |
| JP | 3081666 A2 | 4/1991 |
| JP | 5018959 A2 | 1/1993 |
| JP | 5026875 A2 | 2/1993 |
| WO | WO 03/060517 | 7/2003 |

OTHER PUBLICATIONS

PCT International Search Report dated Oct. 25, 2004.

* cited by examiner

*Primary Examiner*—Walter D Griffin
*Assistant Examiner*—Christine T Mui
(74) *Attorney, Agent, or Firm*—Harold N. Wells

(57) ABSTRACT

A device for detecting an analyte in a fluid sample includes a liquid permeable composition for making a physical separation between compositions of the sample or for reacting with components. The liquid permeable composition has adhesive properties and can be used to make a multi-layered test strip or the composition can be used in the sample wells of microfluidic devices.

50 Claims, 1 Drawing Sheet

LIQUID PERMEABLE COMPOSITION IN DRY REAGENT DEVICES

CROSS-REFERENCE TO RELATED APPLICATION

This application is a continuation-in-part of U.S. application Ser. No. 10/459,825, filed Jun. 12, 2003 now abandoned and claims priority of PCT Application No. PCT/IB03/00055, filed Jan. 13, 2003, which claims priority of Provisional Application No. 60/348,253, filed Jan. 15, 2002.

BACKGROUND OF THE INVENTION

Diagnostic dry reagent analytical devices are common products used in clinical settings for urinalysis and blood testing, particularly glucose monitoring. Results are obtained instrumentally or visually as thresholds and quantitative outputs. Dry reagent analytical devices typically involve absorbent pads containing dispersed reagent systems which react with analytes (components to be detected) in fluid test samples applied to the device to provide a detectable response. These reagents contain indicator dyes, metals, enzymes, polymers, antibodies and various other chemicals dried onto carriers. Carriers often used are papers, membranes or polymers with various sample uptake and transporting properties.

Some reagent strips use only one reagent area to contain all chemicals needed to generate color response to the analyte. In some cases, up to five competing and timed chemical reactions are occurring within one reagent layer. Hemastix® reagent strips (Bayer), a method for detecting blood in urine, is an example of multiple chemical reactions occurring in a single reagent. The analyte detecting reaction is based on the peroxidase-like activity of hemoglobin that catalyzes the oxidation of a indicator, 3,3',5,5'-tetramethyl-benzidine, by diisopropylbenzene dihydroperoxide. In the same pad, a second reaction occurs to remove ascorbic acid interference, based on the catalytic activity of a ferric-HETDA complex that catalyzes the oxidation of ascorbic acid by diisopropyl-benzene dihydroperoxide.

Typical chemical reactions occurring in dry reagent strips can be grouped as dye binding, enzymatic, immunological, and REDOX catalysis. Dye binding to analytes such as albumin leads to color changes at micromolar levels. Indicator dyes can be covalently bound to the analyte (diazonium compounds binding bilirubin) or tightly associated to the analyte (sodium sensing indicators). Enzymatic reactions can be used for the detection of enzymes at micromolar levels through reactions with color forming substrates. Enzymatic reactions can also be used for the detection of molecules, such as glucose, through reactions with enzymes to yield colored end products. Particle labeled antibodies are the primary reagents that provide for the detectable reaction of immunologic strips based on chromatography. REDOX catalysis involves the use of metal chelates to oxidize or reduce indicators in the presence of specific analytes such as hemoglobin and can detect molecules down to the nanomolar level. Certain of these devices involve an enzymatic reaction with the analyte in the presence of a peroxidase and a hydroperoxide to cause a detectable color change in a redox dye and are normally based on the use of filter paper as the absorbent pad.

Dry reagent device designs often include multiple reagent layers to measure one analyte. This change allowed chemical reagent systems to be placed into distinct reagent layers and provided for reaction separation steps such as chromatography and filtration. Immuno-chromatography strips are constructed with chemical reactions occurring a distinct layers of reagents. The CLINITEST® hCG strip test (Bayer) for human chorionic gonadotropin is an example of a dry reagent strip test with four reagent layers. The first layer at the tip of the strip is for sample application and overlaps the next reagent layer, providing for transfer of the patient sample (urine) to the first reagent area. The treated sample then migrates across a third layer, where reactants are immobilized for color development. This migration is driven by a fourth pad that takes up the excess specimen. The chromatography reaction takes place in the third layer, called the test or capture zone, typically a nitrocellulose membrane. In the first and second layers, an analyte specific antibody reacts with the analyte in the specimen and is chromatographically transferred to the nitrocellulose membrane. The antibody is bound to colored latex particles as a label. If the sample contains the analyte, it reacts with the labeled antibody. In the capture zone, a second antibody is immobilized in a band and captures particles when analyte is present. A colored test line is formed. A second band of reagent is also immobilized in the capture zone to allow a control line to react with particles, forming color. Color at the control line is always formed when the test system is working properly, even in the absence of hCG in the patient sample.

Whole blood glucose strips often use multiple reagents to trap intact red blood cells that interfere with the color generation layer. One example is GLUCOMETER Encore® (Bayer), which uses a trapping layer placed directly over the color-generating layer. The color is read from the bottom of the strip through a transparent window. Other designs allow the sample to migrate to a color-generating layer aside from the trapping layer and color is read from the top of the strip. Whole blood test strips often use plastic cassettes to hold the reaction layers in place. Multiple layers of reagent have also been applied to film slides such as the reagent system used with the Ektachem analyzer (Vitros) developed by Eastman Kodak Company (1980). Slides were able to use multiple separating, spreading and color forming layers to enhance colors.

These dry reagent devices are inexpensive and convenient to use but suffer from certain limitations. For example, immunoassays require separation of ingredients to operate, which is often achieved by protein binding. Migration of reagents and analytes often presents problems, leading to inaccurate results. The connections between layers are critical to obtaining accurate results and often fluid transfer between these layers is difficult to control. In the dry reagent format, such as that described by Greenquist in U.S. Pat. No. 4,806,311, an analyte is bound to a labeled reagent and then passed to a detection zone where the amount of the analyte is measured by the amount of labeled reagent. Unreacted labeled reagent is immobilized by immobilized analyte in the reagent zone. Any labeled reagent-analyte which passes into the detection zone is prevented from back migration by being immobilized in the detection zone.

The assembly and fabrication of multilayered devices has not been completely successful. In EP 0226 465 A2 and U.S. Pat. No. 3,992,158 for example, films have been used to separate layers of reagents. However, these devices require tight control of the pore size and shape and of the thickness of the films. One consequence of such designs is that the reagents cannot be on filter paper, since such papers do not have the well defined pore structures of films or the uniform surfaces needed for uniform thickness. But, filter paper is desirable in multilayered devices since they are well suited for use with many reagents due to their inert nature and high water absorbtivity. Thus, filter paper has been used, along with a nylon mesh covering. Such devices rely on surface contact between the reagent layers and this causes reagents to mix on the surface into one layer. The present invention avoids this result and keeps the reagents in their intended positions.

There are many examples of incompatible chemicals in dry reagent systems. For example, the base in white blood cell reagents causes premature hydrolysis of protease substrate. Iron in occult blood reagents causes premature oxidation of redox dye indicators to their colored form, which is also the result of the presence of iodate in glucose reagents. In the case of copper based tests for creatinine, the copper can oxidize redox indicators such as tetramethylbenzidine to their colored form in the absence of creatinine. Tests for occult blood in urine can be skewed by the presence of ascorbate in the urine test sample which acts as a reducing agent to cause false negative results and urine protein tests can be rendered inaccurate by the presence of buffers in the urine sample being tested. Dry assay devices for determining white blood cells in urine can be influenced by interference due to proteins in the urine sample and whole blood assays, such as blood glucose and blood CKMB, suffer from interference caused by red blood cells. In one embodiment, the present invention provides a means for alleviating these problems by separating two layers of a dry reagent device, at least one of which layers contains a reagent for detection of an analyte, with a test fluid permeable composition comprising a blend of an aqueous based polymer dispersion and a water soluble polymer, which blend has been cast and dried to form a layer having adhesive properties.

Previous methods for dealing with these problems have involved separating the reagents into discrete, stacked layers. There are, however, problems associated with the use of the discrete, stacked layer configuration. Thus, the top layer(s) must allow the test sample to pass to the lower layers while continuing to separate certain interfering chemicals and/or biochemicals. For example, metals such as copper or iron should be separated from redox indicators and bases from protease substrates. Oxidants such as iodate and reactants such as ascorbate need to be separated from redox indicators such as tetramethylbenzidine.

These problems are effectively dealt with by derivatizing the permeable composition of the present invention with elements which serve to remove interfering substances as they flow through the first layer of the device, through the permeable composition and into the device's second layer. This multi-layered format requires a permeable, adhesive material to hold the reagent layers together.

However, in the prior art, the contact between the layers was either insufficient to allow the reactants to pass from one layer to the adjacent layer when that was desired, or the reactants migrated from one layer to another when that was not desired.

There are various diffusable, adhesive compositions which can be used to secure two layers in integrated, multilayered reagent devices. Verbeck, in U.S. Pat. No. 3,993,451 uses adhesives to secure reagent containing particles to a substrate layer. The particles may be covered with a porous layer through which a component contained within a sample may pass to reach the reagent containing particles. In the device proposed by Verbeck, the adhesive is not used as a layer which separates reagent layers from detecting layers. Furthermore, the solid particles form separate detecting units which do not rely on movement of the reaction product with an analyte into an adjacent layer for detection.

Japanese Published Application 5-18959 A2 discloses the use of a hydrophobic polymer which does not swell in water as an adhesive to secure reagent layers and Japanese Published Application 5-26875 A2 discloses the use of a porous layer comprising a fluorine containing polymer as an adhesive to secure reagent layers. The polymers used in these Japanese systems are hydrophobic and consequently, they hinder rapid movement of sample fluids through the layers. For rapid testing, the sample fluid should pass through the layers of the device within less than one second. A water soluble adhesive would permit rapid movement of the sample fluid, but would cause the layers to separate as the adhesive begins to dissolve.

In EP 0 226 465 A2 a multilayer analytical device is described in which several porous sheets are bonded together with an adhesive placed so as to form openings through which liquids could pass. The adhesive itself was not capable of passing liquids so that openings were provided instead. The result being that not all of the available surface is useful and contact between the layers is not uniform.

The Greenquist '311 patent mentioned above also discloses a multilayer device for medical testing. Although the concept is valuable, in practice the multilayer device is not as satisfactory as would be desired. The layers must perform their intended function without interfering with the functioning of the adjacent layers. At the same time, the sample fluid must pass rapidly through the layers so that a result can be determined rapidly. Thus, the layers must act independently while not limiting the movement of the sample fluid. The present inventors have overcome these problems, as described below in a multilayer device and also in microfluidic devices.

In U.S. Pat. No. 4,824,640 a transparent layer is disclosed which is useful for containing analytical reagents which consists of a water soluble or water swellable component and an essentially insoluble film forming component. A similar layer is employed in U.S. Pat. No. 6,187,268 B1 as an overcoat over a dry reagent layer.

Dry reagent strips of the sort described above are not the only method of testing used near the patient. Microfluidic devices have been and are being developed which have advantages over multi-layered dry reagent strips. The general principles of certain microfluidic devices of interest to the present inventors is found in U.S. patent application Ser. No. 10/082,415. Microfluidic devices are designed to receive small liquid samples, e.g., blood and urine, and then process the samples through chambers interconnected by capillary passageways. The chambers may contain reagents which react with components in the sample as required for the intended analyses. The difficulties inherent in multi-layered test strips can be avoided. The needed reactions can occur sequentially, as the sample or portions of the sample are moved from one chamber to another, typically by capillary or centrifugal forces. Thus, as will be described in more detail below, the present invention may be applied in microfluidic devices in addition to multi-layered dry test strips.

SUMMARY OF THE INVENTION

The present invention includes methods and devices for the detection of an analyte in a liquid sample which include a liquid permeable layer capable of acting as an adhesive disposed between absorbent layers or non-absorbent layers where at least one of three layers contains reagents. The liquid permeable adhesive layer is permeable to components of the fluid sample and comprises a blend of an aqueous based polymer dispersion and a water soluble polymer which has been cast, dried, and pressed to form a layer which serves as an adhesive. In one embodiment, the liquid permeable adhesive layer is disposed between at least a first absorbent layer and a second absorbent layer in a reagent well in a microfluidic chip or cassette device. At least one of the layers contains a reagent system for the detection of the analyte. In another embodiment, the liquid permeable adhesive layer is disposed between two non-absorbent layers in a reagent well in a microfluidic chip or cassette device. In yet another embodiment, the liquid permeable layer is disposed between multiple alternating absorbent or non-absorbent layers in a reagent well in a microfluidic chip or cassette device. In all embodiments absorbent and adhesive layers can contain or lack reagents.

The water dispersible polymer may be either an anionic or cationic polyurethane dispersion, preferably an anionic polyurethane, in combination with a water soluble polymer, preferably a polyethylene oxide, a polyvinyl pyrrolidone, or a polyvinyl alcohol. The permeable layer is cast on one adjacent layer, then partially dried and pressed onto a second adjacent layer under conditions that cause the permeable layer to adhere to the adjacent layers.

The liquid permeable composition used in the present invention can be used to construct several types of multilayer devices, which include the liquid permeable composition between two absorbent or non-absorbent layers. Liquid permeable composition, having adhesive properties, holds discrete layers together. One layer can be a plastic support, either a base or cover, such as a strip handle, a cassette top or bottom, or a microfluidic cover or base, so that the person using the device can avoid direct contact with the sample fluid. Since the adhesive composition is permeable, it allows reagents and components of the fluid test sample to flow from one layer to another layer.

A multi-layer device can be made so that when a fluid sample is placed on the first absorbent layer, it is spread across the surface of the layer without interacting with the components of the sample. Alternatively, a first absorbent layer may react with interfering components of the sample, permitting the component to be measured (the analyte) to pass through the liquid permeable layer to the second absorbent layer. Or, the first absorbent layer may react with the analyte, which is measured in place or the reaction product may pass through the liquid permeable layer to the second absorbent layer, where it is detected. The second absorbent layer may absorb and retain a component of the fluid sample which has passed through the adhesive layer or it may contain a reagent which reacts with the analyte or the reaction product of the analyte received from the first absorbent layer. The liquid permeable layer can be made so that it prevents the passage of components of the sample by physical separation. Thus, it may serve to concentrate the analyte by passing it while preventing other components from reaching the second absorbent layer. Alternatively, the liquid permeable layer may contain reagents which chemically react with certain of the sample components. In one embodiment, the liquid permeable layer passes certain components of the sample, leaving the more concentrated analyte on the first absorbent layer.

In preferred embodiments the permeable adhesive layer can contain exchange resins and ascorbate scavengers to remove buffering and ascorbate interference from the test sample. The cation exchange resins may include those with oxidative anions such as bromate, iodate, periodate, and chromate or those containing polysulfonic acids, polycarboxylic acids, or polyphosphonic acids with transition metal oxidants such as iron, cobalt, or copper. The permeable adhesive layer can also contain protein binding polymers to separate interfering proteins or antibodies from the sample as well as fillers such as $TiO_2$ or $BaSO_4$ to adjust the opacity or reflectance behavior of the reagent device. Suitable protein binding polymers include, for example, positively charged polymers such as polyamines and polyamides and negatively charged polymers such as polysulfonic, polycarboxylic, and polyphosphonic acids. These polymers may be incorporated into the permeable layer by mixing into the adhesive formula and coating onto the reagent layers.

In microfluidic devices the liquid permeable composition may be disposed in wells in the device to permit passage of a liquid sample or only components thereof. In some embodiments, the multi-layered devices described above may be adapted to function in sample wells in the microfluidic device. In other embodiments the liquid permeable composition may be positioned at the inlet or outlet side of a sample well, or they may fill the well. In such applications, the liquid permeable composition may contain additives to react with components in the sample in order to prepare the sample for further reactions, as in the multi-layered strips described above.

DESCRIPTION OF THE INVENTION

Layer Materials

Three general types of materials are used in layered dry reagent strips or in microfluidic chips for analysis of liquid biological samples, particularly blood and urine. These three materials can be deployed in many configurations, depending on the requirements of the analysis that is to be carried out. They will be generally referred to as absorbent, non-absorbent, and permeable materials.

Biological samples are generally aqueous so that absorbent layers will have the ability to absorb aqueous materials. Thus, they can be classified as generally hydrophilic. Useful materials for absorbent layers include cellulose, nitrocellulose, nylon, glass, porous polyethylene, and polyester. When a biological sample is placed on an absorbent layer, the liquid sample will migrate throughout the layer, as limited by the amount of the sample and the reaction of the sample with reagents which have been placed in or on the absorbent layer. If only one reagent has been applied to the absorbent layer, it will be important to distribute the sample uniformly, so that a consistent response is obtained. If more than one reagent is applied to the absorbent layer, the sample must contact each of the reagents, either at the same time or sequentially if required. Some or all of the sample will migrate to the side opposite to that on which it was placed, thus providing at the opposite face components of the original liquid sample and any mobile reaction products.

Non-absorbent layers, by definition, will not absorb biological samples and often will be hydrophobic, although a non-porous plastic film for example could be hydrophilic and not absorbent. Typically, samples placed on the surface of non-absorbent layers will migrate to the extent that the difference between the surface energies of the sample and the non-absorbent layer allow. Often, the surface is hydrophobic so that liquid samples can be confined to predetermined regions on the layer. For example, reagents may be applied to areas on the non-absorbent layer positioned so that portions of the sample cannot migrate between such areas.

A permeable layer has the ability to transmit liquid from one layer to another, but in a different manner than the absorbent layer described above. The permeable layer is not porous, but its composition can be adjusted so that liquid can migrate through it at differing rates, which will depend on the analysis being carried out. The permeable layer will have intimate contact with adjacent absorbent or non-absorbent layers in many applications, so that the liquid sample, or portions thereof, can be efficiently transferred across the permeable layer to another adjacent surface. Such close contact with adjacent layers will provide adhesion between layers in many applications, which is an advantage when multi-layered test strips are assembled, or when the permeable material is used in microfluidic chips to secure reagent-containing layers in the desired locations.

Multi Layer Devices

Figure 1:
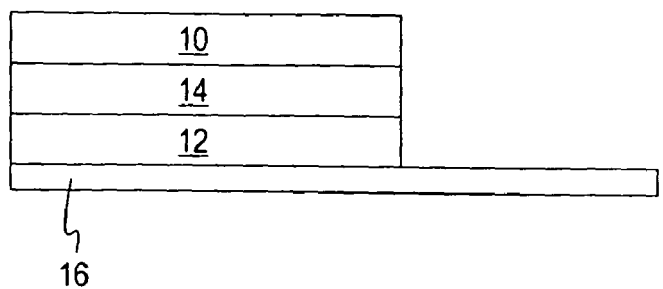
FIG. 1 is a sectional view of a dry reagent device with three layers: a absorbent top layer, an liquid permeable adhesive layer, and an absorbent bottom layer.

In one simple example illustrated in FIG. 1, a multi-layer device for detecting an analyte (i.e. a substance to be detected) in a fluid sample includes a first absorbent layer 10 for receiving a fluid sample, a second absorbent layer 12 for receiving and absorbing a portion of the sample from the first absorbent layer, and a liquid permeable layer 14 disposed between the two absorbent layers, and serving also as an adhesive to hold the absorbent layers together. The liquid permeable layer not only binds the absorbent layers together, but it is capable of reacting with components of the fluid sample to prevent their passage or to physically block passage of components of the fluid sample. The three layers are attached to handle 16. Additional absorbent layers and liquid permeable layers may be added as needed to carry out any particular analysis, as will be evident to those skilled in the art.

The first absorbent layer has several possible functions. It may merely absorb a fluid sample and spread it across the surface of the liquid permeable and adhesive layer. Alternatively, it may react with interfering components of the sample, with the analyte passing through the liquid permeable layer to the second absorbent layer. In another alternative, the first absorbent layer may react with the analyte, which is then measured in place, or the reaction product is passed through the liquid permeable layer to the second absorbent layer for detection.

The second absorbent layer also has several possible functions. It may absorb a portion of the sample passed through the liquid permeable layer, thereby concentrating the analyte in the first absorbent layer. Alternatively, it may receive a portion of the sample including the analyte and then react with the analyte to provide a product which is measured. In another alternative, the second absorbent layer may receive the reaction product produced in the first absorbent layer and concentrated by passage through the liquid permeable layer.

The liquid permeable layer is capable of making a physical separation of the fluid sample, either passing the analyte and preventing other components from passing through to the second absorbent layer or passing interfering components to concentrate the analyte. In other applications, the liquid permeable layer may react with certain components of the sample, thus trapping them in the liquid permeable layer. Or, it may contain additives capable of reacting with certain components and thereby blocking their passage through the liquid permeable layer.

Those skilled in the art will appreciate that this broad description of the function of a multi-layer device of the invention can apply to many alternative specific applications, some of which are discussed below, although others not mentioned are potentially useful analytical methods, while not departing from the broad description of the invention.

Figure 2:
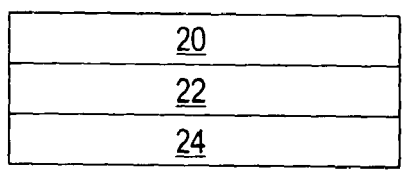
FIG. 2 is a sectional view of a dry reagent device with three layers: a non-absorbent top layer, an liquid permeable adhesive layer, and a non-absorbent bottom layer.

Furthermore, non-absorbent layers may be included in multi-layer devices where appropriate to carry out the analytical procedure of interest. FIG. 2 illustrates one possible configuration. A first non-absorbent layer 20 is used to direct fluid flow between a second non-absorbent layer 24 through the liquid permeable layer 22, which in-turn provides liquid access between layers 20 and 24.

Microfluidic Devices

In another embodiment of the invention, microfluidic devices employ the liquid permeable composition with dry reagents. Microfluidic devices may be referred to as "chips". They are generally small and flat, typically about 1 to 2 inches square (25 to 50 mm square) or circular discs of similar size (e.g., 25 to 120 mm radius). The volume of samples supplied to the microfluidic chips will be small. For example, they will contain only about 0.3 to 1.5 µL. The wells that receive the sample liquids will be relatively wide and shallow in order that the samples can be easily seen and measured by suitable equipment. Capillary passageways interconnecting the wells will have a width in the range of 10 to 500 µm, preferably 20 to 100 µm, and the shape will be determined by the method used to form the passageways. The minimum permitted depth of the passageways may be determined by the properties of the sample. The depth should be at least 5 µm, but at least 20 µm when whole blood is the sample. If a segment of a capillary is used to define a predetermined amount of a sample, the capillary may be larger than the passageways between reagent wells.

While there are several ways in which the capillaries and sample wells can be formed, such as injection molding, laser ablation, diamond milling or embossing, it is preferred to use injection molding in order to reduce the cost of the chips. Generally, a base portion of the chip will be cut to create the desired network of sample wells and capillaries and then a top portion will be attached over the base to complete the chip.

The chips are intended to be disposable after a single use. Consequently, they will be made of inexpensive materials to the extent possible, while being compatible will the reagents and the samples which are to be analyzed. In most instances, the chips will be made of plastics such as polycarbonate, polystyrene, polyacrylates, or polyurethane, alternatively, they may be made from silicates, glass, wax or metal.

For any given passageway, the interaction of a liquid with the surface of the passageway may or may not have a significant effect on the movement of the liquid. When the surface to volume ratio of the passageway is large i.e. cross sectional area is small, the interactions between the liquid and the walls of the passageway become very significant. This is especially the case when one is concerned with passageways with nominal diameters less than about 200 µm, when capillary forces related to the surface energies of the liquid sample and walls predominate. When the walls are wetted by the liquid, the liquid moves through the passageway without external forces being applied. Conversely, when the walls are not wetted by a liquid, the liquid attempts to withdraw from the passageway. These general tendencies can be employed to cause a liquid to move through a passageway or to stop moving at the junction with another passageway having a different cross-sectional area. If the liquid is at rest, then it can be moved by applying a force, such as the centrifugal force. Alternatively other means may be used, including air pressure, vacuum, electroosmosis, absorbent materials, additional capillarity and the like, which are able to induce the needed pressure change at the junction between passageways having different cross-sectional areas or surface energies. When the passageways are very small, capillary forces make it possible to move liquids by capillary forces alone, without requiring external forces, except for short periods when a capillary stop must be overcome. However, the smaller passageways inherently are more likely to be sensitive to obstruction from particles in the biological samples or the reagents. Consequently, the surface energy of the passageway walls is adjusted as required for use with the sample fluid to be tested, e.g. blood, urine, and the like. This allows more flexible designs of analytical devices to be made.

The capillary passageways may be adjusted to be either hydrophobic or hydrophilic, properties which are defined with respect to the contact angle formed at a solid surface by a liquid sample or reagent. Typically, a surface is considered hydrophilic if the contact angle is less than 90 degrees and hydrophobic if the contact angle is greater than 90°. Preferably, plasma induced polymerization is carried out at the surface of the passageways. The analytical devices of the invention may also be made with other methods used to control the surface energy of the capillary walls, such as coating with hydrophilic or hydrophobic materials, grafting, or corona treatments. It is preferred that the surface energy of the capillary walls is adjusted, i.e. the degree of hydrophilicity or hydrophobicity, for use with the intended sample fluid. For example, to prevent deposits on the walls of a hydrophobic passageway or to assure that none of the liquid is left in a passageway.

Movement of liquids through the capillaries may be prevented by capillary stops, which as the name suggests, prevent liquids from flowing through the capillary. If the capillary passageway is hydrophilic and promotes liquid flow, then a hydrophobic capillary stop can be used, i.e. a smaller passageway having hydrophobic walls. The liquid is not able to pass through the hydrophobic stop because the combination of the small size and the non-wettable walls results in a surface tension force which opposes the entry of the liquid. Alternatively, if the capillary is hydrophobic, no stop is necessary between a sample well and the capillary. The liquid in the sample well is prevented from entering the capillary until sufficient forces is applied, e.g. centrifugal force, to cause the liquid to overcome the opposing surface tension force and to pass through the hydrophobic passageway. Centrifugal force in needed only to start the flow of liquid. Once the walls of the hydrophobic passageway are fully in contact with the liquid, the opposing force is reduced because presence of liquid lowers the energy barrier associated with the hydrophobic surface. Consequently, the liquid no longer requires centrifugal force in order to flow. While not required, it may be convenient in some instances to continue applying centrifugal force while liquid flows through the capillary passageways in order to facilitate rapid analysis.

When the capillary passageways are hydrophilic, a sample liquid (presumed to be aqueous) will naturally flow through the capillary without requiring additional force. If a capillary stop is needed, one alternative is to use a narrower hydrophobic section which can serve as a stop as described above. A hydrophilic stop can also be used, even through the capillary is hydrophilic. One such stop is wider than the capillary and thus the liquid's surface tension creates a lower force promoting flow of liquid. If the change in width between the capillary and the wider stop is sufficient, then the liquid will stop at the entrance to the capillary stop. It has been found that the liquid will eventually creep along the hydrophilic walls of the stop, but by proper design of the shape this movement can be delayed sufficient so that stop is effective, even though the walls are hydrophilic. Alternatively a hydrophilic stop can be the result of a abrupt narrowing of the passageway so that the liquid does not flow through the narrow passageway until appropriate force, such as centrifugal force, is applied.

Figure 3:
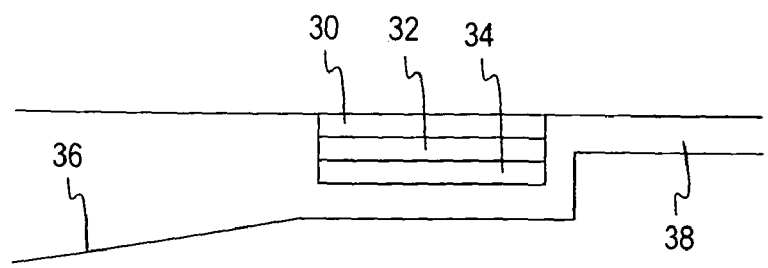
FIG. 3 is a sectional view of a reagent well in a microfluidic chip, containing a layered reagent.

Microfluidic devices may be designed in many ways to carry out analyses of the sort currently carried out with the multi-layered strips described above. Alternatively, since the sample wells are separated in microfluidic devices, it is possible to minimize undesirable interactions between components in liquid samples or the reagents used to carry out the analyses. In some cases, a well will contain a single reagent, intended to carry out one step of the analytical process. However, in the present invention, the liquid permeable composition may be used in various ways, some of which are similar to the multi-layered applications. For example as illustrated in FIG. 3, the liquid permeable composition 32 could be placed between two dry reagents 30 and 34 in a single well. The liquid sample would flow up ramp 36 and contact the three layer reagents, while the air in the reagent well is purged through vent 38. Alternatively, the liquid permeable composition could be deposited at the inlet or the outlet of a sample well to perform a filtering function, that is to remove some components of the sample before reaching a reagent. Further, the entire sample well could be filled with the liquid permeable composition, if desired. Other possible uses include filling in the capillary with liquid permeable composition and adding the additional layers of absorbing and/or non-absorbing materials for the adhesive to bond to inside the device. For example, a well could contain ten very thin layers with permeable adhesive between each layer. The sample flow could be directed to predetermined areas in each layer by the placement of absorbing and non-absorbing materials. The adhesive properties are useful in assuring that the composition remains in position, avoiding movement which could cause the sample to bypass it.

Liquid Permeable Adhesive Composition

The basic elements of the liquid permeable composition useful in the present invention involve an aqueous based polymer dispersion and a water soluble polymer. The permeability of the composition can be adjusted by varying the ratio of the polymer dispersion to the water soluble component. Typically, this ratio will range from 50:1 to 1:1 on a weight basis with a ratio of 10:1 to 5:1 excess of the film forming polymer dispersion being preferred. An increase in the water dispersible polymer will increase the membrane's permeability, which is desirable when faster flow is desired. Conversely, increasing the concentration of the water soluble polymer will decrease the membrane's permeability in cases where greater contact, and accordingly more mixing of the reagents, is desired. In diagnostic dry reagent test devices they allow penetration of the components present in the fluid test sample through the permeable layer binding the reagent layers of the device together. In microfluidic devices, the liquid permeable composition has similar functions, although it may not always be in contact with the dry reagents.

Polyurethane dispersions are preferred for use as the dispersible polymer due to their adhesive properties, flexibility and diverse structures. The reaction of a diisocyanate with equivalent quantities of a bifunctional alcohol provides a simple linear polyurethane. These products are unsuitable for use in the manufacture of coatings, paints and elastomers. However, when simple glycols are first reacted with dicarboxylic acids in a polycondensation reaction to form long chain polyester-diols and these products, which generally have an average molecular weight of between 300 and 2000, are subsequently reacted with diisocyanates the result is the formation of high molecular weight polyester urethanes.

Polyurethane dispersions have been commercially important since 1972. Polyurethane ionomers are structurally suitable for the preparation of aqueous two phase systems. These polymers, which have hydrophilic ionic sites between predominantly hydrophobic chain segments are self dispersing and, under favorable conditions, form stable dispersions in water without the influence of shear forces and in the absence of dispersants. In order to obtain anionic polyurethanes, such as Bayhydrol DLN, which are preferred for use in the present invention, diols bearing a carboxylic acid or a sulfonate group are introduced and the acid groups are subsequently neutralized, for example, with tertiary amines. Sulfonate groups are usually built via a diaminoalkanesulfonate, since these compounds are soluble in water. The resulting polyurethane resins have built ionic groups which provide mechanical and chemical stability as well as good film forming adhesive properties.

Cationic polyurethane dispersions such as Praestol E 150 from Stockhausen Chemical Co. may also be used in forming the liquid permeable composition. One method of preparing cationic polyurethanes is by the reaction of a dibromide with a diamine. If one of these components contains a long chain polyester segment, an ionomer is obtained. Alternatively, polyammonium polyurethanes can be prepared by first preparing a tertiary nitrogen containing polyurethane and then quaternizing the nitrogen atoms in a second step. Starting with polyether based NCO prepolymers, segmented quaternary polyurethanes are obtained.

The most important property of polyurethane ionomers is their ability to form stable dispersions in water spontaneously under certain conditions to provide a binary colloidal system in which a discontinuous polyurethane phase is dispersed in a continuous aqueous phase. The diameter of the dispersed polyurethane particles can be varied between about 10 and 5000 nm. Polyurethane dispersions which are ionic with the ionic radicals being sulphonate, carboxylate or ammonium groups are particularly suitable.

Also suitable for use in the present invention are other film forming polymer dispersions such as those formed by polyvinyl or polyacrylic compounds, e.g. polyvinylacetates or polyacrylates, vinyl copolymers, polystyrenesulfonic acids, polyamides and mixtures thereof. By combining the polymer dispersion with a water soluble polymer there is formed a matrix which forms a swellable network like web. The tighter the web, the smaller the pores and the slower the flow of the test fluid through the matrix.

As water soluble polymers the known polymers such as, for example, polyacrylamides, polyacrylic acids, cellulose ethers, polyethyleneimine, polyvinyl alcohol, copolymers of vinyl alcohol and vinyl acetate, gelatine, agarose, alginates and polyvinylpyrrolidone are suitable. This second polymer component is sometimes referred to as the swelling component due to its swellability by absorbing water. Polyethyleneoxides, polyvinylpyrrolidones and polyvinylalcohols are preferred. These polymers can vary widely in molecular weight so long as they are water soluble and miscible with the aqueous polymer dispersion. Polyethylene oxides of a molecular weight from 300,000 to 900,000 g/mol and polyvinylpyrrolidone having a molecular weight of from 30,000 to 60,000 g/mol are particularly suitable. The molecular weight of the water soluble polymer is not critical so long as they are miscible with the polymer dispersion and allow the incorporation of assay specific reagents such as buffers, indicators, enzymes and antibodies. The finished film should be swellable so as to be permeable to the test fluid.

The polymers are dispersed/dissolved in a solvent (preferably aqueous) preparatory to its application to the dry reagent device or microfluidic chip by use of a dispenser as in the following examples. In the preferred aqueous casting solutions, aqueous polymer dispersions are mixed with an aqueous solution of the second polymer such as, for example, polyvinyl acetate dispersions with cellulose ethers, polyurethane dispersions with polyvinyl alcohol, polyurethane dispersions with gelatine or polyurethane dispersions with polyvinylpyrrolidone. Normally, a surfactant is added to the formulation to enhance its spreadability and a thickener such as silica gel is added to thicken the formulation to a consistency which facilitates it being spread across a surface. The formulation is then applied to the dry reagent device or microfluidic chip, such as by a Myer rod applicator or a wiped film spreader, and dried to remove solvent. Typical dry thicknesses of the permeable membrane range from 1 to 100 mils (0.0254 to 2.54 mm).

As will be shown in Example VI below, the permeable layer, which must adhere to adjacent layers, requires that certain processing conditions are used during lamination of multi-layer devices of the invention. More particularly, for a given thickness, the temperature used to initially dry the permeable layer and the pressure used to laminate the device were interrelated with the thickness of the wet as-applied layer. In general, a thin layer should not be exposed to high temperatures for long periods, while a thicker layer is more tolerant. Also, some pressure must be applied to the partially dried permeable layer to assure that it adheres to the adjacent layers. Neither thin (e.g. 1 mil) nor thick (e.g. 100 mil) layers will adhere without some pressure being applied. That is, the permeable layer does not behave like more familiar adhesives. However, when pressure is applied (e.g. 2 to 150 psi) the permeable layer acts as an adhesive, provided that it has not been exposed to temperatures that result in excessive drying of the wet layer. Thus, the correct combinations of wet layer thickness, temperature, and pressure are needed to provide the multi-layer device of the invention.

The preferred formulations for the permeable layer, such as those used in the examples that include polyurethane dispersions combined with polyethylene oxide, will be applied as a wet layer having a thickness of about 1 to 100 mils. They will be dried at a temperature of about 40 to 90° C., but not higher than the temperature at which the polyurethane dispersion is fully dried, say about 110° C. The temperature is chosen such that the permeable layer is not completely dried, which will depend upon the thickness applied. Pressure is applied to the assembled device while the permeable layer remains incompletely dried, followed by a period of ambient temperature drying. The pressure used will depend on the method of application, but may be as low as 2 psi. Typically, 3 to 150 psi will be used, but above about 200 psi it may be difficult to avoid extruding the permeable layer from between the adjacent layers.

Use of the Liquid Permeable Composition

Protein interference in an assay for white blood cells in urine is alleviated by the protein sticking to the liquid permeable composition and not passing through the reagent. Buffer interference in tests for urine protein is reduced by either adhering to the liquid permeable composition (ion pairing) or being neutralized (proton exchange) with the result being either that the buffer does not come into contact with the reagent or is altered to a non-interfering form which matches the pH of the reagent. The instability of reagents for testing urine creatinine due to the presence of incompatible chemicals when all are mixed in one discrete reagent layer is prevented by the liquid permeable composition, since a device can be fabricated to hold two discrete reagent layers, one with copper and the other with a redox indicator. The copper is kept separated from the redox indicator until it comes into contact with the fluid test sample. The sample provides creatinine to bind with the copper and the copper is liberated from the top layer and mixed with the redox indicator.

Ascorbate interference with urine occult blood tests can be alleviated by incorporating ascorbate scavengers, such as a metal capable of oxidizing ascorbate bound to a polymer, into the liquid permeable. Polymer bound metal ascorbate scavengers are described in U.S. Pat. No. 5,079,140. Other oxidizing agents such as iodate and persulfate can be immobilized within the permeable composition to serve as ascorbate scavengers.

The liquid permeable composition can be used advantageously in conjunction with immunoformats to provide sensitive assays for various analytes. For example, a transparent membrane for use in a multi-layered device can be prepared with an immobilized anti-binding label antibody contained therein. Typically, this antibody will be immobilized within the membrane by attaching it to a larger entity such as a latex particle which is incorporated into the polymer blend which forms the membrane before it is cast onto the reagent device. Thus, when the binding label on the anti-analyte antibody has the fluorescein structure, such as in the case of fluorescein isothiocyanate (FITC), anti-FITC can be interspersed within the permeable membrane to capture FITC labeled anti-analyte antibody. In addition, anti-analyte antibody labeled with a peroxidase is incorporated into the membrane, so that as test fluid flows through the membrane, analyte contained therein will bind with bound anti-analyte antibody and peroxidase labeled anti-analyte antibody to form a sandwich attached to the membrane, thereby preventing the peroxidase from reaching the reagent layer, which contains a peroxide and a redox dye, and providing a colored response. In this embodiment, the response produced by the interaction of the analyte, peroxidase, peroxide and redox dye is inversely proportional to the concentration of the analyte in the fluid test sample.

More generally, non-limiting examples of reagents which may find use in multi-layer or microfluidic devices according to the invention include the following:

reagents for reaction with an analyte in the first absorbent layer which receives the fluid sample may include enzymes such as oxidases, reductases, and proteases commonly used in clinical assays; affinity binders such as antibodies, nucleic acids, antigens, and proteins such as are used in both binding assays and reactions in which the analyte is converted to a detachable chemical.

reagents for reaction with an interfering component of the fluid sample may include enzymes to metabolize the interferent, reactants to convert interferent to non-reactive form, and binding agents to trap the interferent.

reagents for reaction with an analyte in the second absorbent layer may include indicators producing signals in response to the analyte and enzymes or reactants for signal amplification.

reagents for reaction with an analyte in the second absorbent layer which analyte had been reacted in the first absorbent layer and passed through the adhesive layer include enzymes used in clinical assays and affinity binders used in binding assays and reactions in which a moiety of the analyte is detached.

additives to the liquid permeable composition capable of reacting with components of said sample include affinity binders or enzymes for removing interferents or generating signals.

The examples provided below illustrate alternative embodiments of the invention, although it is not intended to be limited only to these examples. In one example, a layer of filter paper is treated with a reagent solution for the analyte which is to be detected. The treated filter paper is then coated with an adhesive layer of the invention and a second layer of untreated filter paper is added, which can serve to concentrate the reagent which has reacted with the analyte and then migrates through the adhesive layer into the untreated filter paper. In a second example, an adhesive layer includes a material which prevents migration of interfering compounds through the adhesive layer into the reagent layer. A third example includes a top layer with a reagent for the analyte. The product of the reaction of the analyte and reagent passes through the adhesive layer and is detected in the bottom layer.

Example I

A diffusible adhesive was prepared as follows:

(1) 75 g of a 50 mM monobasic phosphate buffer (Fisher, pH 7.0) and 0.5 g of a Pluronic P75 surfactant (BASF) were added to a 250 mL steel beaker. Then while stirring slowly 0.3 g of octanol followed by 5.0 g of Aerosil 200 silica gel (DeGussa AG) were added to the beaker. The stirring rate was increased to about 2000 rpm for several minutes to achieve complete dispersion of the contents of the beaker.

(2) Stirring was continued for about 15 minutes while 40.25 g of a 40 wt % aqueous solution of Bayhydrol D-762 (polyester polyurethane resin, Bayer Corporation) followed by 0.2 g of polyethylene oxide, m.w. 900,000 were added.

(3) The coating solution was stirred under a slight vacuum for several minutes to de-gas the solution, after which it was ready to cast on a reagent layer. An albumin reagent layer was prepared by:

(1) Preparing two solutions for sequential application to a filter paper base. The compositions are given in the following table:

| Ingredient | Function | Pref. Conc. Used | Allowable Range |
|---|---|---|---|
| *Albumin Reagent Composition* | | | |
| *1st application* | | | |
| Water | Solvent | 1000 mL | — |
| Tartaric add | Cation Sensing Buffer | 93.8 g (625 mM) | 50-750 mM |
| Quinaldine red | Background dye | 8.6 mg (12 μM) | 5-30 μM |
| *2nd application* | | | |
| Toluene | Solvent | 1000 mL | — |
| DIDNTB | Buffer | 0.61 g (0.6 mM) | 0.1-3.0 mM |
| Lutonal M40 | Polymer enhancer | 1.0 g | 0.54 g/L |

DIDNTB = 5'.5'-Dinitro-3'.3'-Diiodo-3.4,5.6-Tetrabromophenosulfonephthalein (2). Filter paper (Whatman GF/30 cm) was treated with the two solutions in sequence to saturate the paper, after which the treated filter paper was dried for 15 minutes at 90° C. to produce the top layer reagent.

The adhesive coating solution was cast on the albumin reagent layer to a wet thickness of about 250 μm, after which the adhesive coated albumin reagent on the filter paper was dried at about 90° C. for about 5 minutes.

A complete format was assembled in which a layer of glass filter paper (Whatman GF/30 cm) was placed on the opposite side of the adhesive layer from the albumin reagent layer. That is, a test device contained three layers, i.e. an albumin reagent layer, a diffusible adhesive layer, and a layer of glass filter paper. This test device was compared with an albumin reagent layer made as described above, but which was not coated with the diffusible adhesive layer.

In the first test, a sample containing 500 mg/L of albumin was applied to the albumin reagent layer without an adhesive coating and the result was compared with another 500 mg/L sample placed on the glass filter paper of the composite device. In the later case the albumin would have to pass through the filter paper and the adhesive layer to reach the reagent layer where it would be detected. In the comparative sample, the reagent layer would give an immediate response. The amount of albumin present was determined by reflectance measurement using a CLINITEK 200 instrument. When no sample had been added to the albumin reagent layer, the reflectance was 93.6% at a wave length of 610 nm at 1 minute from beginning of the analysis. However, when the sample was added directly to the reagent layer without an adhesive layer the reflectance was found to be 12.8%. The reflectance was found to be 13.0% when the sample was applied to the glass filter paper and reached the reagent layer by passing through the paper and the adhesive. It can be concluded that the filter paper and the adhesive had substantially no effect on the composition of the sample, which passed through them and reached the reagent layer.

In a second test, a much smaller concentration of albumin was used, 1 mg/L. In this case the albumin reagent without an adhesive coating showed a reflectance of 52.4%, indicating the smaller concentration of albumin in the sample. However, when a sample was placed directly on the albumin reagent layer in the composite device, the reflectance was measured to be 25.4%, indicating a higher response to the same concentration of albumin. It can be concluded that some of the liquid in the sample passed through the adhesive and into the filter paper layer, thus raising the effective concentration of albumin on the reagent layer.

Example II

In this example, a binding reagent layer is added to the diffusible adhesive layer to remove either a competing or interfering component, thus permitting the analyte to reach the detecting reagent layer. A protein blocked diffusible adhesive composition was made in a similar manner to the adhesive composition described in Example I, as follows:

(1) To a 250 ml steel beaker was added 150 g of 0.1 m sodium citrate buffer having a pH of 5.5 and 1.0 g of Pluronic L64 surfactant. With slow stirring 0.6 g of octanol was added followed by 12.0 g of Aerosil 200 and stirring continued for several minutes at about 2000 rpm to complete the dispersion of the ingredients.

(2) With continued stirring 110 g of a 40% aqueous solution of Bayhydrol DLN was added followed by 0.4 g of PEO 900,000. Mixing continued for about 15 minutes.

(3) For each gram of the coating solution completed in step (2), 100 µL of a casein blocking solution was added. The mixture was vortexed in order to produce a homogenous coating solution. The adhesive coating solution was cast onto a peroxidase reagent layer. The peroxidase reagent layer was prepared by:

(a) preparing a 10 mg/mL solution of 3,3',5 5'tetraethylbenzidine, (b) dipping a Whatman 3 mm filter paper into the solution, (c) drying the impregnated paper for 15 minutes at a temperature of 40° C.

(d) dipping the dried paper of step (c) in a solution of 1400 U/mL of stock glucose oxidase, and (e) drying the impregnated paper of step (d) for 20 minutes at 40° C.

(4) The adhesive-peroxidase reagent layer combination was pressed with a pressure of about 3 psi onto a binding reagent layer, the binding reagent was prepared by:

(a) making a polymer membrane from the following components 17.3 g Dralon L (polyacrylonitrinle)

69.1 g Ultrason E (polyetherpolysulfone)

25.9 g Aerosil 200 (silica)

7.78 Pluriol P 600 (propylene oxide-based surfactant (b) dipping the membrane into a solution of 4 mg/mL anti-FITC (anti-fluorescein isothiocyanate) in 0.1 M sodium citrate pH 4.5 buffer, and (c) Drying the impregnated filter paper for 30 minutes at 40° C.

(d) Drying the treated membrane for 30 minutes at 40° C.

(5) The combined layers were dried at room temperature for 1-2 hours to complete preparation of the analytical device.

In a test, the sample contained both BSA-FITC (bovine serum albumin-anti-fluorescein isothiocyanate) and HRP-FITC (horseradish peroxidase-anti-fluorescein isothiocyanate), the later competing with the BSA-FITC. As the sample passes through the adhesive layer, there is a separation of BSA-FITC from the HRP-FITC. The HRP-FITC which reaches the peroxidase reagent and a color is developed, indicating its presence and is measured by reflectance on a CLINITEK® 50 analyzer. When only HRP-FITC was present, the reflectance was found to be 62.6%, while when BSA-FITC was present the reflectance was 45.7%, indicating that HRP-FITC is capable of passing through the membrane when an excess of FITC is achieved A comparative test was made in which the binding layer and the peroxidase reagent layer were placed in contact with each other without the intermediate adhesive layer. In that case, there was no difference observed between the two samples. That is, there was no separation of the sample containing both BSA-FITC and HRP-FITC. It can be concluded that it was not possible without the adhesive to keep the competing analyte separated, even though an excess of FITC was present in the binding layers.

Example III

This example illustrates the use of a multi-layer device similar to that of Example II for measuring digoxin. The reagent containing a substrate capable of detecting peroxidase and the protein binding layer were prepared as described in Example II. Then, those layers were placed on either side of a diffusible adhesive layer previously described to produce a three-layer device. The combined layers were cut into strips, each strip being covered with a polystyrene strip having square openings which served as sample wells. Test samples were prepared containing 0, 25, 50, and 100 µg/mL of digoxin and 50 ml of a 50 mg/ml solution digoxin-BSA-HRP (digoxin-bovine serum albumin-horseradish peroxidase), and 50 mg of a 100 µg/ml solution of anti-digoxin labeled FITC. 45 µL of each sample mixture was added to a sample well on a strip to bring the sample into contact with the protein binding layer. The sample passed through the top layer and the adhesive layer into the reagent layer where a color response was developed. Measurements made by a CLINITEK® 50 reflectance spectrometer indicated that the digoxin was reaching the reagent layer proportionally to its concentration in the sample, as shown in the following table.

TABLE 3

| Con. of Digoxin in Test Sample | % Reflectance |
| --- | --- |
| 0 | 85% |
| 25 | 65% |
| 50 | 51% |
| 100 | 40% |

In a comparative test in which no adhesive layer was included, no variation in response was found from the reagent layer, indicating that without the adhesive layer competition did not take place.

Examples IV and V illustrate the use of a multi-layer device similar to that of Example II for measuring glucose with the use of a microfluidic chip as the holder for the reagent.

Example IV

An example of using the permeable adhesive in a microfluidic device is in measuring the glucose content of blood. A glucose reagent as described in Bell U.S. Pat. No. 5,360,595 is prepared on an absorbent layer, e.g., a nylon membrane such as Biodyn from Pall Corp. The permeable adhesive formula as described in Example 1 is then coated on the top of the glucose reagent. A area of the reagent is placed in a microfluidic reagent well with permeable adhesive being face up or face down. When face down, the adhesive bonds with the microfluidic base and when face up the adhesive makes a bond with a non-absorbent plastic lid covering the chamber. Other layers of absorbent or non-absorbent materials also can be applied as layers.

Samples of blood containing a concentration of glucose are introduced into the reagent chamber using an inlet port. The whole blood sample reacts with the reagent to provide a color, which is then read on a spectrometer at 680 nm, as corrected against a black and white standard.

Example V

A glucose reagent as described in Bell U.S. Pat. No. 5,360,595 is prepared by coating reagent onto plastic non-absorbent substrates such as PES and PET. Where PET coated with reagent is used, a 500 nm to 950 nm transmittance meter is used to read the reaction with the sample. The permeable adhesive is coated on the top of the glucose reagent as flow through the permeable adhesive is allowed. The adhesive bonds to the microfluidic base, a non-absorbent plastic lid covering the chamber, or other layers of absorbent or non-absorbent materials as long as the flow of sample from the inlet port to the reagent is unobstructed by non-absorbing materials. Samples of blood containing a concentration of glucose are introduced into the reagent chamber using an inlet port. The whole blood sample reacts with the reagent to produce a color. Since the plastic films are transparent, a 500 nm to 950 nm transmittance meter is used to read the reaction with the sample, as corrected against a black and white standard.

Example VI

A composition similar to that of Example I was deposited on a bottom layer of filter paper and a top layer of either filter paper or PET was applied. After applying the permeable adhesive composition to the bottom layer of filter paper, the composition was initially cured at either 40° C. for 20 minutes or at 90° C. for 5 or 10 minutes in an oven. Thereafter, the top layer of filter paper or PET was applied and laminated onto the adhesive layer using a roller laminator at 100 ft/minute and an applied force of either 0 psi or 40-100 psi and with no applied heat. After lamination, the combined three layers were cured at substantially ambient temperature for 2 hours to complete hardening. The results are shown in the following table.

| Case | Temp/time | Lamination pressure (psi) | Thickness Mil (μm) | Tear Seal | Bubbles | Permeability | Delaminating | Double side adhesion |
| --- | --- | --- | --- | --- | --- | --- | --- | --- |
| 1 | 90 C./5 min | 0 | 10 (254) | YES | NO | Good | NO | NO |
| 2 | 40 C./20 min | 0 | 10 (254) | NO | YES | Good | YES | NO |
| 3 | 90 C./5 min | 0 | 100 (2540) | YES | YES | Poor | NO | NO |
| 4 | 40 C./20 min | 0 | 100 (2540) | NO | NO | Good | YES | NO |
| 5 | 90 C./5 min | 100 | 10 (254) | YES | NO | Good | NO | NO |
| 6 | 40 C./20 min | 100 | 10 (254) | YES | NO | Good | NO | YES |
| 7 | 90 C./5 min | 100 | 100 (2540) | YES | NO | Good | NO | YES |
| 8 | 40 C./20 min | 100 | 100 (2540) | YES | NO | Good | NO | YES |
| 9 | 40 C./10 min | 0 | 3 (75) | NO | YES | Good | YES | NO |
| 10 | 40 C./10 min | 100 | 3 (75) | YES | NO | Good | NO | YES |

In the above table, the characteristics of the laminated layers are:

Tear Seal refers to whether the adhesion to the bottom layer of filter paper is strong enough to cause failure to occur within the filter paper rather than in the adhesive layer.

Bubbles refers to formation of areas in which the adhesive did not adhere, as determined by applying water to one of the outer layers to detect areas in which the adhesive did not adhere to the outer layer.

Permeability was determined by applying water to one of the outer layers and measuring the time required for the water to reach the other layer.

Delaminating refers to an evaluation of the separation between the layers when the three layers are cut, punched, and pressed in commercial equipment.

Double Side Adhesion is related to the Tear Seal evaluation. If a tear seal occurs between the bottom filter paper and the adhesive, but the top layer does not adhere to the adhesive, then it is reported that double side adhesion has not been achieved. If the top layer does adhere to the adhesive, then double side adhesion is reported.

The results shown in the Table show that both pressure and temperature affected the ability to achieve double-side adhesion of the composition, while retaining good permeability. Thickness of the composition layer affected both permeability and adhesion. By applying pressure and adjusting the curing temperature, the desired permeability and double side adhesion could be achieved, as shown by Cases 6-8 and 10.

Cases 1-4 and 9 show that pressure is needed to achieve double side adhesion. Drying temperature and thickness of the as-applied layer are shown in cases 5-8 to be interdependent.

What is claimed is:

1. A device for detection of an analyte in a liquid sample comprising:
   a liquid permeable layer for transferring portions of said liquid sample,
   two adjacent layers in contact with and adhering to said liquid permeable layer, at least one of said adjacent layers containing reagents for detecting said analyte,
   said liquid permeable layer comprising a blend of an aqueous polymer dispersion and a water soluble polymer applied as a coating on one of said two adjacent layers and dried at a temperature of about 40° C. to 90° C. to form a dried liquid permeable layer having a dried thickness of about 3 to 100 mils (75 to 2540 µm),
   said dried liquid permeable layer on one of said two adjacent layers having been pressed together with the second of said two adjacent layers with a pressure of about 3 to 100 psi sufficient to cause said two adjacent layers to adhere to said liquid permeable layer, and
   the pressed liquid permeable layer and two adjacent layers having been further cured such that the pressed liquid permeable layer adheres to said two adjacent layers while retaining liquid permeability.

2. A device of claim 1 further comprising additives in said liquid permeable layer or said two adjacent layers which chemically react with components in said liquid sample.

3. A device of claim 2 wherein said additives include indicator dyes or particles to provide a detectable response with said analyte.

4. A device of claim 2 wherein said additives include exchange resins to remove buffering components and ascorbate scavengers to remove ascorbate interference.

5. A device of claim 2 wherein said additives include particles and polymers to provide a detectable response or remove interfering components.

6. A device of claim 2 wherein said additives include metals and chelates to provide a detectable response or remove interfering components.

7. A device of claim 2 wherein said additives include enzymes to provide a detectable response or remove interfering components.

8. A device of claim 2 wherein said additives include antibodies or other affinity molecules to provide a detectable response or separate interfering components.

9. A device of claim 2 wherein said additives include fillers to adjust opacity or reflectance.

10. A device of claim 2 wherein said additives include surface active substance to increase fluid flow.

11. A device of claim 1 wherein the liquid permeability of said liquid permeable layer is adjusted by changing the ratio of said aqueous polymer dispersion to said water soluble polymer.

12. A device of claim 11 wherein said aqueous polymer dispersion is a polyurethane dispersion and said water soluble polymer is at least one member of the group consisting of a polyethylene oxide, a polyvinyl pyrrolidone and a polyvinyl alcohol.

13. A device of claim 12 wherein the ratio of said aqueous polymer dispersion to said water soluble polymer is 50:1 to 1:1 on a weight basis.

14. A method of analyzing a liquid sample wherein said sample is contacted with dry reagents in at least one layer containing said reagents which react with analytes in said sample to provide a detectable response, said method characterized by including a liquid permeable layer in contact with and adhering to two adjacent layers, said liquid permeable layer comprising a blend of an aqueous polymer dispersion and a water soluble polymer for transferring portions of said liquid sample between said layers, said liquid permeable layer being applied as a liquid coating on one of said two adjacent layers and dried at a temperature of about 40° C. to 90° C. to form said liquid permeable layer having a dry thickness of about 3 to 100 mils (75 to 2,540 µm), and then pressed together with the other of said two adjacent layers with a pressure of about 3 to 100 psi sufficient to cause said liquid permeable layer to adhere to said adjacent layers and then further dried in place between said two adjacent layers such that the liquid permeable layer adheres to both of said two adjacent layers while retaining liquid permeability.

15. A method of claim 14 wherein said liquid permeable layer concentrates said liquid sample by passing said sample through said liquid permeable layer.

16. A method of claim 14 wherein said liquid permeable layer or said two adjacent layers include additives which chemically react with components in said liquid sample.

17. A method of claim 16 wherein said additives include indicator dyes or particles to provide a detectable response with said analyte.

18. A method of claim 16 wherein said additives include exchange resins to remove buffering components and ascorbate scavengers to remove ascorbate interference.

19. A method of claim 16 wherein said additives include particles and polymers to provide a detectable response or remove interfering components.

20. A method of claim 16 wherein said additives include metals and chelates to provide a detectable response or remove interfering components.

21. A method of claim 16 wherein said additives include enzymes to provide a detectable response or remove interfering components.

22. A method of claim 16 wherein said additives include antibodies or other affinity molecules to provide a detectable response or separate interfering components.

23. A method of claim 16 wherein said additives include fillers to adjust opacity or reflectance.

24. A method of claim 16 wherein said additives include surface active substance to increase fluid flow.

25. A method of claim 14 wherein the liquid permeability of said liquid permeable layer is adjusted by changing the ratio of said aqueous polymer dispersion to said water soluble polymer.

26. A method of claim 25 wherein said aqueous polymer dispersion is a polyurethane dispersion and said water soluble polymer is at least one member of the group consisting of a polyethylene oxide, a polyvinyl pyrrolidone and a polyvinyl alcohol.

27. A method of claim 26 wherein the ratio of said aqueous polymer dispersion to said water soluble polymer is 50:1 to 1:1 on a weight basis.

28. A multi-layer device for detection of an analyte in a fluid sample comprising:

(a) a first layer for receiving said fluid sample;

(b) a second layer for receiving at least a portion of said sample from said first layer; and (c) a liquid permeable adhesive layer disposed in contact with and adhering to said first and second layers, said liquid permeable adhesive layer being diffusible to fluids and comprising a blend of an aqueous polymer dispersion and a water soluble polymer which has been cast as a liquid coating on one of said first and second layers and dried at a temperature of about 40° C. to 90° C. to form said liquid permeable layer having a dry thickness of about 3 to 100 mils (75 to 2,540 μm), then pressed together with the other of said two adjacent layers and dried in place between said first and second layers with a pressure of about 3 to 100 psi sufficient to cause said first and second layers to adhere to said liquid permeable layer and at temperatures such that said adhesive layer adheres to said first and second layers while retaining liquid permeability, at least one of said combined layers of (a), (b), (c) containing reagents and being capable of detecting said analyte.

29. A device of claim 28 wherein said first layer is an absorbent layer which absorbs and spreads said fluid sample over said device.

30. A device of claim 28 wherein said first layer is an absorbent layer which comprises a reagent for reaction with an analyte in said sample.

31. A device of claim 28 wherein said first layer is an absorbent layer which comprises a reagent for reaction with interfering components of said sample.

32. A device of claim 28 wherein said second layer is an absorbent layer which absorbs and retains a component from said sample.

33. A device of claim 28 wherein said second layer is an absorbent layer which comprises a reagent for reacting with an analyte in said sample.

34. A device of claim 31 wherein said component from said sample is the product of a reaction of an analyte in said first absorbent layer.

35. A device of claim 28 wherein said liquid permeable adhesive layer is capable of making a physical separation of said fluid sample.

36. A device of claim 28 wherein said liquid permeable adhesive layer is capable of reacting with components of said sample and thereby trapping them in said liquid permeable adhesive layer.

37. A device of claim 28 wherein said liquid permeable adhesive layer contains additives capable of reacting with components of said sample and thereby preventing their passage through said liquid permeable adhesive layer.

38. A device of claim 28 wherein said liquid permeable adhesive layer is an anionic polyurethane dispersion in combination with a water soluble polymer.

39. A device of claim 28 wherein said liquid permeable adhesive layer is an anionic polyurethane dispersion in combination with a cationic acrylic dispersion as the water soluble polymer.

40. A device of claim 28 wherein said liquid permeable adhesive layer is a cationic polyurethane dispersion in combination with a water soluble polymer.

41. A device of claims 38 or 40 wherein said water soluble polymer is at least one member of the group consisting of a polyethylene oxide, a polyvinylpyrrolidone and a polyvinylalcohol.

42. A device of claim 29 wherein said first absorbent layer is a filter paper.

43. A device of claim 30 wherein said reagent for reaction with an analyte in said first absorbent layer is a member of the group consisting of oxidases, reductases, and proteases used in clinical assays, and antibodies, nucleic acids, antigens, and proteins used in binding assays.

44. A device of claim 31 wherein said reagent for reaction with an interfering component of said sample is a member of the group consisting of enzymes to metabolize the interferent, reactants to convert the interferent to non-reactive form, and binding agents to trap the interferent.

45. A device of claim 32 wherein said second absorbent layer is a filter paper.

46. A device of claim 33 wherein said reagent for reacting with an analyte in said second absorbent layer is a member of the group consisting of indicators producing signals in response to the analyte and enzymes or reactants for signal amplification.

47. A device of claim 34 wherein said product of the reaction of an analyte in said first absorbent layer is detected by a member of the group consisting of enzymes used in clinical assays and affinity binders used in binding assays and reactions in which a moiety of the analyte is detached.

48. A device of claim 37 wherein additives to said liquid permeable adhesive layer capable of reacting with components of said sample are members of the group consisting of affinity binders or enzymes for removing interferents or generating signals.

49. The device of claim 28 further comprising additional absorbent layers disposed between said first and second layers, each of said additional absorbent layers being separated from the closest neighbor layer by an additional liquid permeable adhesive layer, said liquid permeable adhesive layer being diffusible to said fluid sample and comprising a blend of an aqueous polymer dispersion and a water soluble polymer which has been cast, pressed, and dried to form said adhesive layer while retaining permeability.

50. A method of detecting an analyte in a fluid sample comprising applying said fluid sample to a multi-layer device of claim 28 and measuring the amount of analyte present in said sample.

* * * * *